United States Patent
Yi et al.

(10) Patent No.: US 9,694,033 B2
(45) Date of Patent: Jul. 4, 2017

(54) IL-9 SECRETING CD8+ TC9 CELLS AND METHODS OF TREATING CANCER

(71) Applicant: THE CLEVELAND CLINIC FOUNDATION, Cleveland, OH (US)

(72) Inventors: Qing Yi, Cleveland, OH (US); Yong Lu, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 159 days.

(21) Appl. No.: 14/605,112

(22) Filed: Jan. 26, 2015

(65) Prior Publication Data

US 2015/0209388 A1 Jul. 30, 2015

Related U.S. Application Data

(60) Provisional application No. 61/931,084, filed on Jan. 24, 2014.

(51) Int. Cl.
| | | |
|---|---|---|
| A61K 35/00 | (2006.01) | |
| A61K 35/17 | (2015.01) | |
| A61K 31/675 | (2006.01) | |
| C12N 5/0783 | (2010.01) | |

(52) U.S. Cl.
CPC .......... *A61K 35/17* (2013.01); *A61K 31/675* (2013.01); *C12N 5/0638* (2013.01); *C12N 2501/15* (2013.01); *C12N 2501/2302* (2013.01); *C12N 2501/2304* (2013.01); *C12N 2501/2312* (2013.01); *C12N 2501/24* (2013.01)

(58) Field of Classification Search
CPC ...... A61K 35/17; A61K 31/00; A61K 31/675; C12N 5/0638
See application file for complete search history.

(56) References Cited

U.S. PATENT DOCUMENTS

| | | |
|---|---|---|
| 7,442,507 B2 | 10/2008 | Polsky et al. |
| 7,572,631 B2 | 8/2009 | Berenson et al. |
| 2008/0279813 A1 | 11/2008 | Hall et al. |
| 2014/0186295 A1 | 7/2014 | Kupper et al. |

FOREIGN PATENT DOCUMENTS

| | | |
|---|---|---|
| WO | 2004048557 A1 | 6/2004 |
| WO | 2008033403 A2 | 3/2008 |
| WO | 2008141275 A1 | 11/2008 |

(Continued)

OTHER PUBLICATIONS

Lu et al., (J Clin Invest. Nov. 1, 2012; 122(11): 4160-4171. ePub Oct. 15, 2012).*

(Continued)

*Primary Examiner* — Cherie M Stanfield
(74) *Attorney, Agent, or Firm* — Tarolli, Sundheim, Covell & Tummino LLP

(57) ABSTRACT

A method of producing a population of CD8+ Tc9 lymphocytes is provided including priming a population of naïve CD8+ T cells by contacting the population of naïve CD8+ T cells with an immunogenic peptide, in the presence of a Tc9 supportive environment, thereby producing a population of CD8+ Tc9 lymphocytes which secrete IL-9. Purified populations of CD8+ Tc9 cells are also disclosed herein, as are method for their use in the treatment of cancer in a subject.

11 Claims, 13 Drawing Sheets

(56) References Cited

FOREIGN PATENT DOCUMENTS

| WO | 2009073513 A1 | 6/2009 |
|---|---|---|
| WO | 2009131712 A2 | 10/2009 |
| WO | WO 2012129394 A9 * | 9/2012 |
| WO | 2014030001 A1 | 2/2014 |

OTHER PUBLICATIONS

Jager et al., (J Immunol Dec. 1, 2009;183(11):7169-77. epub Nov. 4, 2009).*
Desfrancois et al., (PLoS One. Jan. 2010; 5:1(e8437. pp. 1-10).*
Sevko et al., (J Invest Dermatol. Jun. 2013;133(6):1610-9. Epub Dec. 6, 2012).*
Cho et al., (J Immunol Dec. 1, 2013, 191 (11) 5559-5573).*
Kamimura et al., (J Exp Med. Aug. 6, 2007;204(8):1803-12. Epub Jul. 30, 2007).*
Cho et al., (J Exp Med. Aug. 21, 2000;192(4):549-56).*
Lu, Yong, et al. "Tumor-specific IL-9-producing CD8+ Tc9 cells are superior effector than type-I cytotoxic Tc1 cells for adoptive immunotherapy of cancers." Proceedings of the National Academy of Sciences 111.6 (2014): 2265-2270.
Purwar, Rahul, et al. "Robust tumor immunity to melanoma mediated by interleukin-9-producing T cells." Nature medicine 18.8 (2012): 1248-1253.
Visekruna, Alexander, et al. "Tc9 cells, a new subset of CD8+ T cells, support Th2-mediated airway inflammation." European journal of immunology 43.3 (2013): 606-618.

* cited by examiner

IL-9 SECRETING CD8+ TC9 CELLS AND METHODS OF TREATING CANCER

RELATED APPLICATION

This application claims priority from U.S. Provisional Application No. 61/931,084, filed Jan. 24, 2014, the subject matter of which is incorporated herein by reference in its entirety.

GOVERNMENT FUNDING

This invention was made with government support under CA200539 awarded by the National Institutes of Health. The government has certain rights in the invention.

TECHNICAL FIELD

This application relates to IL-9 secreting CD8+ Tc9 cells, pharmaceutical compositions comprising the same, and methods for producing, formulating or using the same to treat cancer is subjects in need thereof.

BACKGROUND OF THE INVENTION

Adoptive cell therapy (ACT) using ex vivo differentiated type-I CD8+ cytotoxic T (Tc1) cells has shown significant clinical promise for the treatment of established cancers. Recent clinical trials using ACT combined with lymphodepletion have resulted in objective responses in 50-70% of patients with advanced melanoma. However, complete responses remain infrequent with most patients, and improvements to this approach are needed. Current understanding of determinants of successful CD8+ T-cell adoptive therapy includes, but is not limited to, persistence of transferred T cells, differentiation status of transferred T cells, telomere length, and lymphodepleting condition. In particular, administration of naïve or early effector T cells in combination with active immunization and IL-2 can result in eradication of large established tumors.

Cytokine priming signals direct CD8+ T cells to acquire unique profiles that affect their ability to mediate specific immune responses. CD8+ T cells can acquire cytokine secreting phenotypes that require transcription factors similar to those of T helper (Th) cells. Tc1 cells secrete IFN-γ and kill tumor targets by releasing cytotoxic molecules such as GrzB and Perforin. The contribution of adoptively transferred Tc1 cells in antitumor responses has been clearly established, and Tc1 has stronger therapeutic effect than Tc2 and regulatory CD8+ T cells. In addition, naïve CD8+ T cells can be differentiated into Tc17 cells in Th17 polarizing conditions. IL-17 and IL-17-producing T cells are tumor-promoting factors and can mediate IL-6-induced Stat3 activation to generate protumorigenic environment, which may limit the application of Tc17 for adoptive therapy.

IL-9 is a pleiotropic cytokine that has direct and indirect effects on multiple cell types. It has recently been reported that Th9 cell-derived IL-9 not only inhibited tumor progression, but also promoted greater tumor clearance than Th1 cells that have traditionally been considered as the most efficient CD4+ T-cell subset to generate antitumor immunity. Nevertheless, identification of CD8+ T-cell subsets with optimal therapeutic potential remains a critical challenge for the advances of cancer immunotherapy.

SUMMARY OF THE INVENTION

This application relates to IL-9 secreting CD8+ Tc9 cells, pharmaceutical compositions comprising the same, and methods for producing, formulating or using the same to treat cancer is subjects in need thereof. One aspect of the application relates to a method of producing a population of CD8+ Tc9 lymphocytes. The method can include priming a population of naïve CD8+ T cells by contacting the population of naïve CD8+ T cells with an immunogenic peptide, in the presence of a Tc9 supportive environment, thereby producing a population of CD8+ Tc9 lymphocytes which secrete IL-9.

A further aspect of the application relates to a method treating cancer in a subject. The method can include administering to the subject a therapeutically effective amount of a population of CD8+ Tc9 cells, wherein the population of CD8+ Tc9 cells secretes IL-9.

BRIEF DESCRIPTION OF THE DRAWINGS

The foregoing and other features of the application will become apparent to those skilled in the art to which the application relates upon reading the following description with reference to the accompanying drawings, in which.

DETAILED DESCRIPTION

Figure 1:
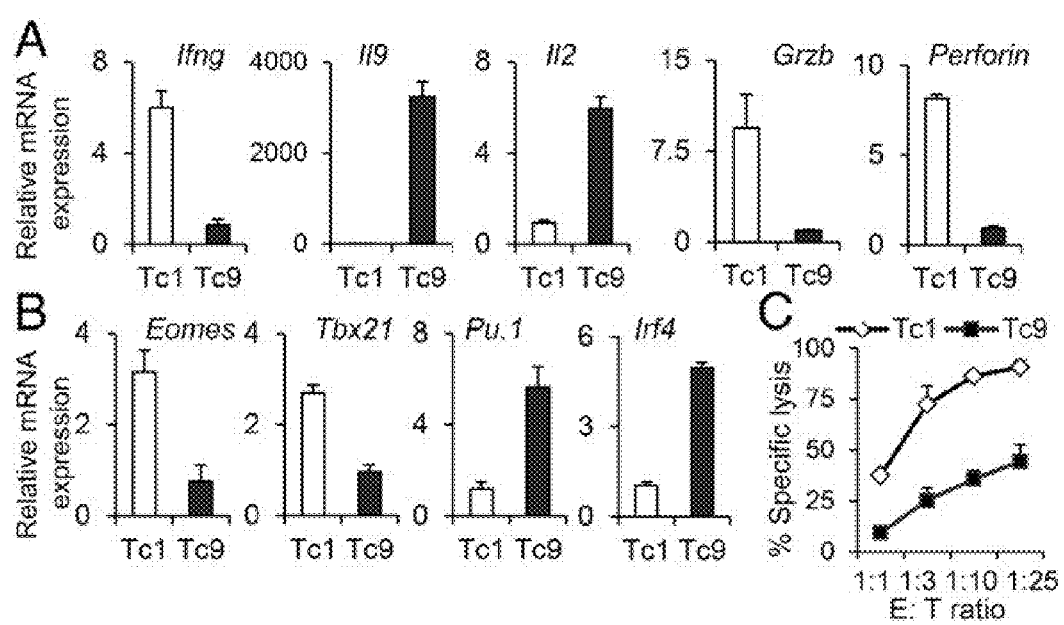
FIG. 1 illustrates Tc9 cells produced IL-9 and were diverted from cytolytic differentiation; (A) is a series of graph showing real-time PCR analysis of relative mRNA expression of cytokines and cytolytic-related molecules in OT-I Tc1 and Tc9 cells; B is a series of graph showing real-time PCR analysis of relative mRNA expression of transcription factors in OT-I Tc1 and Tc9 cells. Expression relative to Gapdh is displayed; (C) is a graph showing percent of specific lysis determined after 8 hours where T cells were added at the indicated ratios to $CFSE^{hi}$ B16-OVA target cells or $CFSE^{lo}$ B16 nontarget cells in duplicate. Representative results from one of two performed experiments are shown.

This application relates to IL-9 secreting CD8+ Tc9 cells, pharmaceutical compositions comprising the same, and methods for producing, formulating or using the same to treat cancer is subjects in need thereof. It has been discovered that differentiation of CD8+ T cells under T helper 9-polarizing conditions induces the development of an IL-9 producing CD8+ T (Tc9) cell subset which elicits a greater antitumor response against large established tumors than classic type-1 CD8+ cytotoxic T cells that are presently used in clinical protocols.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the application.

As used herein, the term "therapeutically effective amount" can refer to that amount of a pharmaceutical composition that results in amelioration of symptoms or a prolongation of survival in a subject. A therapeutically relevant effect relieves to some extent one or more symptoms of a disease or condition or returns to normal either partially or completely one or more physiological or biochemical parameters associated with or causative of the disease or condition.

As used herein, the terms "treating" or "treatment" of a condition or disease can include: (1) inhibiting the disease or condition, i.e., arresting, delaying or reducing the development of the disease or condition and its symptoms; or (2) relieving the disease or condition, i.e., causing regression of the disease or condition and its clinical symptoms. The term "treatment" or "treating", as used herein, does not encompass 100% cure of cancer. However, in one embodiment, the therapeutic methods described herein may result in 100% reversal of disease. As used herein, the terms "prophylactic" or "preventative" treatment can include preventing at least one symptom of the disorder, disease or condition, i.e., causing a clinical symptom to not significantly develop in a subject that may develop or be predisposed to the disease but does not yet experience or display symptoms of the disease or condition. In one embodiment, prophylactic administration of a composition including a population of CD8+ Tc9 cells described herein serves to prevent formation of cancer in a subject.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, "IL-9" refers to a 4-helix bundle cytokine that is produced by T-cells, typically by CD4+ helper cells (e.g. activated Th2 cells, or Th9 cells) but as described herein also in cytotoxic CD8+ Tc9 cells. Alternative names for IL-9 include, but are not limited to, P40, HP40, T-cell growth factor p40, interleukin-9, or P40 cytokine.

As used herein, "adoptive cell transfer" is the process of passively transferring cells, particularly immune-derived cells, into a new host with the goal of transferring the immunologic functionality and characteristics into the new host. In some embodiments, IL-9 producing cells are used in adoptive cell transfer according to the methods described herein. In some embodiments, Tc9 cells are used in adoptive cell transfer according to the methods described herein.

As used herein, the term "peptide" is used to designate a series of residues, typically L-amino acids, connected one to the other typically by peptide bonds between the alpha-amino and carbonyl groups of adjacent amino acids.

An "immunogenic peptide" is a peptide which comprises an allele-specific motif such that the peptide will bind the MHC allele and be capable of inducing a CTL response. Thus, immunogenic peptides are capable of binding to an appropriate MHC molecule and inducing a cytotoxic T response against the antigen from which the immunogenic peptide is derived.

Methods of Producing a Population of CD8+ Tc9

Methods of producing a population of CD8+ Tc9 are provided herein. The method includes priming a population of naïve CD8+ T cells. Naïve CD8+ T cells can be primed by contacting the population of naïve CD8+ T cells with an immunogenic peptide, in the presence of a Tc9 supportive environment, thereby producing a population of CD8+ Tc9 lymphocytes which secrete IL-9.

In some embodiments naïve CD8+ T cells can be obtained from a subject (e.g., a human subject). In certain embodiments, naïve CD8+ T cells can be isolated from a blood sample or spleen collected from a subject, such as a donor or recipient subject, using standard methods including Ficoll density gradient centrifugation followed by negative selection to remove undesired cells. Methods of isolating naïve CD8+ T cells are known to those of skill in the art and include FACS sorting of CD8+ cells. Naïve CD8+ T cells can also be obtained from a subject using an apheresis procedure. In some embodiments, the naïve CD8+ T cells are also L-selectin positive cells (i.e., CD62L+).

In accordance with the method, a population of naïve CD8+ T cells are contacted with an immunogenic peptide in order to prime the naïve T cells. An immunogenic peptide for use in the invention can be prepared synthetically, or by recombinant DNA technology or isolated from natural sources such as whole viruses or tumors. The Tc9 cells produced are typically specific for an antigen present on a tumor (e.g., a solid tumor). Therefore in certain embodiments, the immunogenic peptide is isolated or derived from a tumor (e.g., a subject's cancerous solid tumor).

In some embodiments, the desired immunogenic peptide can be loaded into the binding pockets of MHC molecules on the surface of antigen presenting cells (APCs) using standard methods. In an exemplary embodiment, the APCs are irradiated antigen presenting dendritic cells which become peptide-loaded antigen dendritic cells when loaded with a desired immunogenic peptide. Typically, the antigen presenting cells are irradiated so APCs won't proliferate in response to T cell produced cytokines or other cytokines added to the culture.

In an alternative embodiment, a population of naïve CD+ T cells can be genetically engineered to produce receptors on their surface called chimeric antigen receptors (CARs). CARs are proteins that allow the T cells to recognize a specific protein (antigen) on tumor cells (e.g., a solid tumor cell from a subject having cancer). For example, naïve CD+ T cells T cells can be transfected with and grown to express CARs such that T cells expressing CARs can target and kill tumors via tumor-associated antigens.

Appropriate means for preparing a transduced population of lymphocytes expressing a selected CAR construct will be well known to the skilled artisan, and includes retrovirus, lentivirus (viral mediated CAR gene delivery system), sleeping beauty, and piggyback (transposon/transposase systems that include a non-viral mediated CAR gene delivery system), to name a few examples. Transduced cytotoxic lymphocytes can be grown in Tc9 supportive polarizing conditions described herein that are suitable for a population of cells that will be introduced into a subject such as a human Priming, or stimulation, of the T cells is performed in the presence of a Tc9 supportive environment, which results in the production a population of CD8+ Tc9 lymphocytes which secrete IL-9.

In one embodiment, a Tc9 supportive environment can include a standard T cell culture growth medium such as RPMI-1640 or AIM-V with the addition of an effective amount of Tc9 polarizing cytokines and agents. CD8+ cytotoxic (Tc) cells can differentiate into multiple effector subsets (e.g., Tc1 and Tc2) capable of secreting different cytokine patterns. In accordance with the present invention, Tc9 polarizing cytokines and agents are those cytokines and agents capable of differentiating or "polarizing" CD8+ T cells into a specific Tc effector subset with the specific phenotype of IL-9 secretion. Tc9 polarizing cytokines for use in the present invention include but are not limited to IL-4 and TGF-β. Tc9 polarizing agents can include neutralizing agents such as INF-γ and IL-12 neutralizing agents.

Tc9 supportive environment can include about 1 to about 100 ng/ml of IL-4. In a certain embodiment the Tc9 supportive environment can include about 10 ng/ml of IL-4. A Tc9 supportive environment can include about 0.1 to about 10 ng/ml of TGF-β. In a certain embodiment the Tc9 supportive environment can include about 1 ng/ml of TGF-β.

Tc9 supportive environment can include a neutralizing amount of an INF-γ neutralizing agent and/or a neutralizing amount of an IL-12 neutralizing agent. A neutralizing amount is an amount of an agent sufficient to decrease the activity or amount of a substance to a level that is undetectable using standard methods. For example, a neutralizing amount of an IL-12 or INF-γ neutralizing agent is the amount of agent which decreases the biological activity of IL-12 or INF-γ, for example to an IL-12 or INF-γ activity level below that which can be detected using a standard immunoassay. Such agents can thus be used to inhibit IL-12 or INF-γ activity. Examples of such agents, include, but are not limited to anti-IL-12 or anti-INF-γ antibodies and soluble IL-12 or INF-γ receptors.

In some embodiments a Tc9 supportive environment can include about 1 μg/ml to about 100 μg/ml of anti-IL-12 monoclonal antibodies. In certain embodiments, the IL-12 neutralizing agent includes about 10 μg/ml of anti-IL-12 monoclonal antibodies. In some embodiments a Tc9 supportive environment can include about 1 μg/ml to about 100 μg/ml of anti-INF-γ monoclonal antibodies. In one embodiment, the INF-γ neutralizing agent includes about 20 μg/ml of anti-INF-γ monoclonal antibodies.

In some embodiments, T cell populations described herein are incubated in the Tc9 supportive environment with the appropriate immunogenic peptide-loaded APCs for a time period sufficient to prime the naïve cells. Preferably, however, the CD8+:APC (i.e. responder to stimulator) ratio is in the range of about 10:1 to 100:1. The CTL/APC culture may be maintained for as long a time as is necessary to stimulate a therapeutically useable or effective number of Tc9 cells.

In some embodiments, primed CD8+ Tc9 cells may be effectively separated from the APC using one of a variety of known methods. For example, monoclonal antibodies specific for the APCs, for the peptides loaded onto the stimulator cells, or for the CD8+ Tc9 (or a segment thereof) may be utilized to bind their appropriate complementary ligand. Antibody-tagged cells may then be extracted from the admixture via appropriate means, e.g., via well-known immunoprecipitation or immunoassay methods.

In some embodiments, the primed CD8+ Tc9 cells are further allowed to proliferate in a second fresh Tc9 supportive environment further including IL-2. For example, the expansion step can include adding IL-2 to the Tc9 supportive culture medium (e.g., wherein the concentration of IL-2 is about 1 ng/ml to about 100 ng/ml or preferably about 50 ng/ml). In an exemplary embodiment, the primed population of CD8+ Tc9 cells are allowed to proliferate in a second Tc9 supportive environment for about 3 days prior to therapeutic use.

The cultures described herein can typically be incubated under conditions of temperature and the like that are suitable for the growth and differentiation of CD8+ T lymphocytes. For the growth of human T lymphocytes, for example, the temperature will generally be at least about 25 degrees Celsius, preferably at least about 30 degrees, more preferably about 37 degrees.

In an exemplary embodiment of producing a population of CD8+ Tc9 cells described in the Example below, Tc9 cells are produced by priming naïve CD8+CD62L+ T cells by contacting the naïve cells with irradiated peptide-loaded splenic APCs in the presence of Tc9-polarized medium including IL-4 (10 ng/ml:R&D Systems), TGF-β (1 ng/ml; R&D Systems), anti-IFN-γ monoclonal antibodies (mAbs; 20 µg/ml; eBioscience) and anti-IL-12 mAbs (10 µg/ml; eBioscience). Beginning 2 days after priming, cell culture are expanded in fresh Tc9-polarized medium supplemented with 50 ng/ml IL-2 (50 ng/ml; R&D Systems) for additional 3 days before further use such as administration to a subject in need thereof for the treatment of cancer.

Also comprehended by this disclosure are CD8+ Tc9 cells produced by the methods disclosed herein, as well as compositions containing such cells. In one embodiment, a substantially purified population of CD8+ Tc9 lymphocytes has less than 30% CD4+ cells, for example less than 20% CD4+ cells, such as less than 10% CD4+ cells.

The term "purified" does not require absolute purity; rather, it is intended as a relative term. Thus, for example, a purified cell population of CD8+ Tc9 cells is one in which the percentage of CD8+ Tc9 cells in a population of cells (e.g., in culture) is more pure than CD8+ Tc9 cells in their natural environment, such as within a human subject. In particular examples, substantially purified populations of CD8+ Tc9 cells refers to populations of CD8+ Tc9 cells that are at least 50%, 60%, 65%, 70%, 75%, 80%, 90%, 95%, 96%, 97%, 98% or 99% pure. In one embodiment, a substantially purified population of CD8+ Tc9 cells is composed of at least about 70%, such as at least about 80%, such as at least about 90% CD8+ Tc9 cells. That is, the population of CD8+ Tc9 cells includes less than about 20%, such as at least about 10%, of other T lymphocytes such as Tc1 cells. The purity of a CD8+ Tc9 population can be measured based on cell surface characteristics (e.g. as measured by fluorescence activated cell sorting) or by cytoline secretion profile (e.g. as measured by an ELISA assay), as compared to a control.

Figure 4:
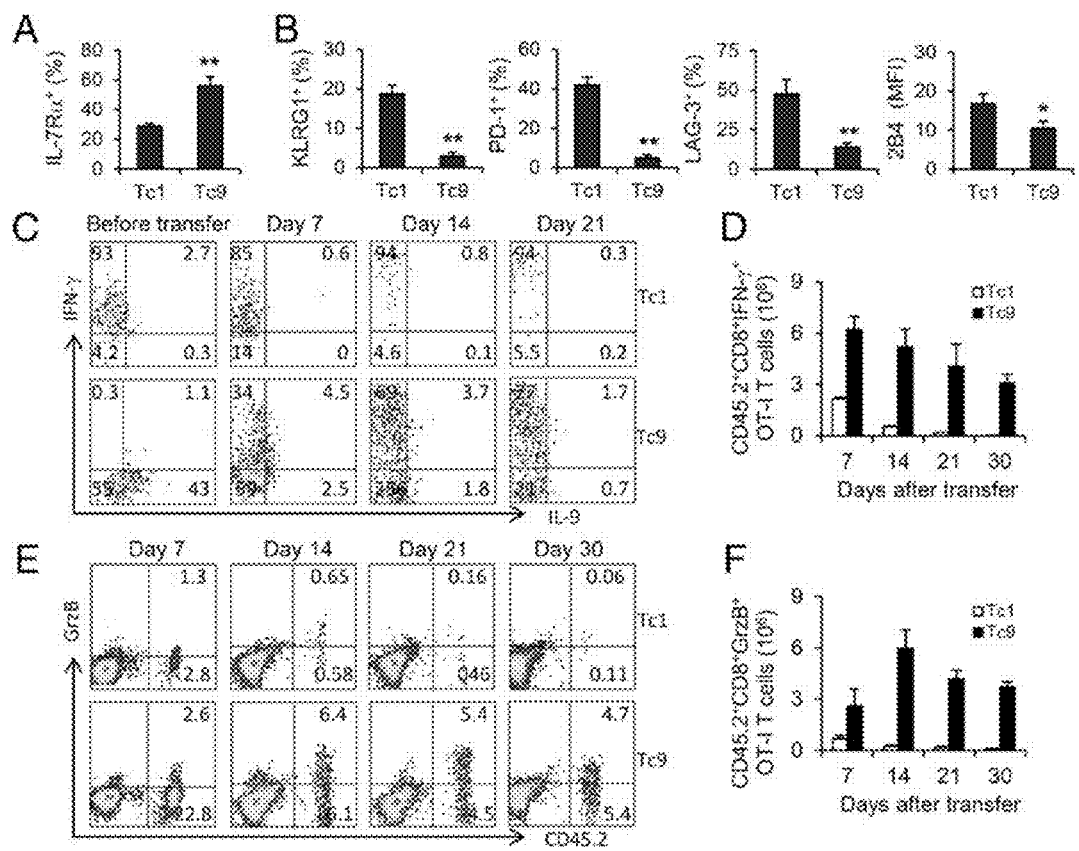
FIG. 4 illustrates that Tc9 cells display less exhausted phenotype and switch to Tc1-like cells in tumor-bearing mice. Tumor-bearing mice (n=3) were transferred with OT-I Tc1 or Tc9 cells and treated the same as described in FIG. 1. Splenocytes were harvested and analyzed; (A) is a graph showing expression of IL-7Rα by transferred cells 7 d after transfer; (B) is a series of graph showing expression of indicated exhaustion markers by transferred cells 7 d after transfer; (C) is a series of histograms showing a FACS determination of intracellular cytokine production by Tc1 or Tc9 cells before and after transfer; (D) is a graph showing the total number of IFN-γ-producing Tc1 or Tc9 cells after transfer was calculated from FACS analysis; (E) is a series of histograms showing a FACS determination of GrzB-producing Tc1 or Tc9 cells after transfer; (F) is a graph showing total number of GrzB-producing Tc1 or Tc9 cells after transfer was calculated from FACS analysis. Representative results from one of two performed experiments are shown. *P<0.05; **P<0.01.

CD8+ Tc9 cell populations produced as described herein can be further characterized by the cytokines secreted or expressed by a portion of the cells. In certain embodiments, Tc9 cell populations produced as described herein secrete IL-4, IL-10 and IL-17. Tc9 cell populations of the present invention can display less exhausted phenotype compared to a Tc1 cell population. For example, in some embodiments, greater than about 40% of cells in a CD8+ Tc9 population secrete IL-7Rα, less than about 10% are PD-1+ and/or KLRG1+, less than about 25% are LAG-3+, and less than 15% of the population are 2B4+(see FIG. 4).

The secretion of cytokines can be measured using standard bioassays, such as an ELISA. For example, fluorescence activated cell sorting can be utilized. Alternatively the supernatant content is tested for secretion of cytokines. In one embodiment, an assay, such as a bioassay, and ELISA, or a radioimmunoassay, is performed to test the cytokine secretion profile of the cells.

The methods disclosed herein can further include cryopreserving the generated CD8+ Tc9 lymphocytes.

The CD8+ Tc9 cell compositions described herein and pharmaceutical compositions including the cell populations can be used in a method for treating cancer in a subject. As less-exhausted younger cells, the sufficient lineage plasticity of CD8+ Tc9 cells allows these cells subsequently to differentiate into long-lasting IFN-γ-producing Tc1-like effector cells upon administration to a subject. Without being bound by theory, it is believed that IL-9 secreted by the Tc9 cells promotes the migration of Tc9 cells into tumor tissues enabling the cells to exert long-lasting antitumor therapeutic effect. Therefore, another aspect of the invention relates to a method of treating a cancer in a subject. The method includes administering to a subject a therapeutically effective amount of a population of CD8+ Tc9 cells produced as disclosed herein, wherein the population of CD8+ Tc9 cells secretes IL-9.

In certain embodiments, a subject in need thereof is administered tumor specific IL-9 producing CD+ Tc9 cells; e.g. cancer specific IL-9 producing cells that are primed using a desire immunogenic tumor derived peptide in the presence of a Tc9 supportive environment and expanded in vitro as described above, prior to administration to patient.

In some embodiments, the Tc9 cells administered to the subject are derived from autologous naïve CD8+ T cells obtained from the subject. For example, a blood sample can be obtained from a subject and naïve CD8+ T cells isolated from the sample. The naïve CD8+ T cells can be contacting the population of naïve CD8+ T cells with an immunogenic Tumor derived peptide, in the presence of a Tc9 supportive environment to produce Tc9 IL-9 secreting cells and then administered to the same subject.

CD8+ Tc9 cells administered to the subject may also be derived from naïve CD8+ T cells obtained from a donor (e.g., either a matched sibling donor or an HLA-mismatched donor that is identified either through a registry or from a non-matched family donor, such as an haplo-identical donor—usually a parent or child of the subject)

The administration of a pharmaceutical composition including IL-9 secreting CD8+ Tc9 cells may be for either "prophylactic" or "therapeutic" purpose. When provided prophylactically, therapy is provided in advance of any symptom. The prophylactic administration of the therapy serves to prevent formation of cancer. Prophylactic administration may be given to a subject at risk of cancer with, for example, a family history of cancer, or a subject that has had a cancer removed surgically. Alternatively, administration of the CD8+ Tc9 cells may be given to a subject with rising cancer marker protein levels. Multiple biomarkers for particular cancers are known in the art. Example melanoma markers are described in PCT Publications WO 2008/141275, WO 2009/073513, or in U.S. Pat. No. 7,442,507.

In one aspect, the method can include administering to the subject a therapeutically effective amount of a pharmaceutical composition comprising a population of CD8+ Tc9 cells described herein and a pharmaceutical carrier. It will also be appreciated that the pharmaceutical carrier can be selected on the basis of the chosen route of administration and standard pharmaceutical practice for adoptive transfer protocols. Suitable carriers and their formulation are described, for example, in the book *Remington's Pharmaceutical Sciences* (Remington's Pharmaceutical Sciences, Mack Publishing Company, Easton, Pa., 1985).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumen.

Pharmaceutical compositions of the application can be administered by any means that achieve their intended purpose. In certain embodiments, administration is intravenous or intratumoral. Cells may be administered systemically, or locally at the site of the cancer.

Methods for administering cells are well known to those of skill in the art e.g. as provided in WO 2004/048557; WO 2008/033403; U.S. 2008/0279813 WO2008/033403; U.S.

Pat. No. 7,572,631; and WO 2009/131712, which are herein incorporated by reference in their entirety. The amount of IL-9 producing CD8+ Tc9 cells which will be effective in the treatment and/or suppression of cancer may be determined by standard clinical techniques. The dosage will depend on the type of cancer to be treated, the severity and course of the cancer, previous therapy the recipient has undertaken, the recipient's clinical history, and the discretion of the attending physician. The IL-9 producing CD8+ Tc9 cell population may be administered in various treatment regimes, e.g., a single or a few doses over one to several days to ameliorate symptoms or periodic doses over an extended time to inhibit cancer progression or to prevent cancer recurrence. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

The cells are generally in a volume of a liter or less, can be 500 ml or less, even 250 ml or 100 ml or less. Hence the density of the desired cells is typically about $1 \times 10^6$ to about $1 \times 10^{12}$, and more preferably about $1 \times 10^8$ to about $1 \times 10^{11}$ CD8+ Tc9 cells are utilized for the treatment of cancer in adult humans, compared to about $5 \times 10^6$-$5 \times 10^7$ cells used in mice. In addition, populations of CD8$^+$ Tc9 lymphocytes can be cryopreserved and thawed prior to administration to a recipient.

The methods described herein are useful for the treatment of any type of cancer in a subject. As used herein, the term "cancer" includes any type of cancer. A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. In some circumstances, cancer cells will be in the form of a tumor; such cells may exist locally within an subject, or circulate in the blood stream as independent cells, for example, leukemic cells. In one embodiment, the cancer may be tumorogenic cancer, i.e. a cancer associated with a tumor, or a skin lesion such as in melanoma.

In certain embodiments, prior to treatment, the patients are selected for having a particular cancer, or for being at risk of a particular cancer. The presence of cancer can be determined by means well known to clinicians. Initial assessment of cancer is based on symptoms presented by the patient. In addition, there are follow-up diagnostic procedures, including, but not limited to PET scans, CAT scans, biopsies, and bio-marker assessments.

Examples of cancer include, but are not limited to, breast cancer, melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

In some embodiments the cancer treated is a solid tumor. Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In particular embodiments, the cancer is a carcinoma solid tumor. For example, the solid tumor can include a renal cell carcinoma, ovarian cancer, breast cancer, colon cancer (adenocarcinoma) or malignant melanoma.

In some embodiments, the methods described herein may be used to treat melanoma. The term "melanoma" as used herein includes all types of melanoma, including, for example, melanoma skin cancer, ocular melanoma, and mucosal melanoma.

In some embodiments, infusion of the CD8+ Tc9 cells into the subject for the treatment of cancer may further include the co-administration of an effective amount T cell growth factor such as IL-2, IL-7 and/or IL-15. In an exemplary embodiment, recombinant human IL-2 (rhIL-2) can be administered at $6 \times 10^5$U i.p. daily for 4 doses after CD8+ Tc9 administration.

In another embodiment, the practice of the method in conjunction with other therapies as a combination therapy is contemplated such as conventional chemotherapy, radiation therapy or surgery directed against solid tumors and for control of establishment of metastases. The administration of therapeutically effective amounts of CD8+ Tc9 cells may be conducted before, during or after chemotherapy, radiation therapy or surgery.

The phrase "combination therapy" embraces the administration of the CD8+ Tc9 cells and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In some embodiments, chemotherapeutic agents, may be used in combination therapy with the CD8+ Tc9 cell populations of the present invention. Exemplary chemotherapeutic agents can include alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

In some embodiments, a chemotherapeutic agent can include, but are not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol.

Figure 5:
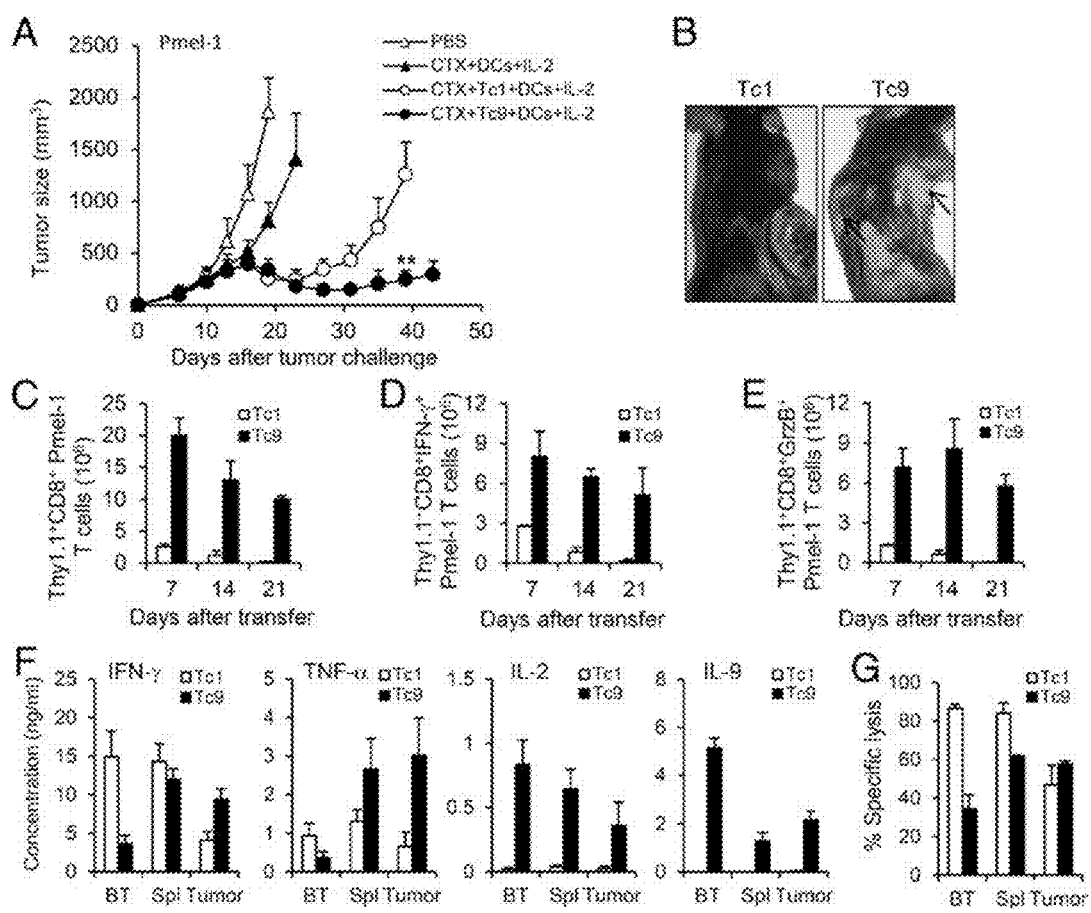
FIG. 5 illustrates that CTX synergizes with Pmel-1 Tc9 cells to control large established B16 melanoma in vivo. Pmel-1 Tc1 or Tc9 cells were primed in polarized conditions and expanded with IL-2. Tc1 or Tc9 cells (2×10$^6$) were adoptively transferred into C57BL/6 mice bearing 10-d large established B16 melanoma. One dose of CTX was given 1 d before T-cell transfer. DC vaccination and IL-2 were administered to some group of mice after T-cell transfer. (A) is a graph showing tumor responses (n=5) to adoptive transfer of Tc1 or Tc9; (B) is an image of a representative autoimmune vitiligo of tumor-bearing mice 25 d after T-cell transfer. Arrows indicated the presence of vitiligo; (C) is a graph showing persistence of transferred Tc1 or Tc9 cells in the spleens of treated tumor-bearing mice analyzed by FACS; (D and E) are graphs showing the total numbers of IFN-γ-producing (D) or GrzB-producing (E) Thy1.1$^+$CD8$^+$ cells after transfer were calculated from FACS analysis; (F) is a series of graphs showing transferred Tc1 or Tc9 cells sorted from the spleens or tumor tissues at day 14 after transfer. The cells were then restimulated with splenocytes pulsed with 0.01 μg/mL hgp100$_{25-33}$ peptide in triplicate for 24 h. Production of indicated cytokines was determined by ELISA. BT represents cells before transfer; (G) is a graph showing transferred Tc1 or Tc9 cells sorted from the spleens or tumor tissues at day 14 after transfer. Cytolytic function of T cells was tested by in vitro cytotoxicity assay at 10 to 1 effector to target ratios with CFSE$^{hi}$ B16 target cells and CFSE$^{lo}$ MC38 nontarget cells in duplicate. Percentage of specific lysis was determined overnight. Representative results from one of two performed experiments are shown. **P<0.01.

In certain embodiments, the chemotherapeutic agent is cyclophosphamide. As shown in FIG. 5, 250 mg/kg of the alkylating agent cyclophosphamide (CTX, Sigma-Aldrich) synergizes with CD8+ Tc9 cells to mediate enhanced anti-tumor immunity. Therefore, in certain embodiments, a combination therapy including CD8+ Tc9 cells and an alkylating agent, such as cyclophosphamide, can be used in for the effective treatment of cancer in a subject, wherein the combination exhibits synergistic therapeutic effects. In some embodiments the CTX is administered i.p. 1 day before CD8+ Tc9 administration in a single dose.

In some embodiments, prior to administration of a population of CD8+ Tc9 cells the subject's immune system, such as T cells, can be non-selectively or selectively depleted, or ablated, by any method known in the art, for example, selective depletion or ablation of T cells or a specific subset of T cells. Exemplary treatments to induce lymphopenia in a subject prior to CD8+ Tc9 administration can include but are not limited to the administration of chemotherapeutics and/or total body irradiation.

In one embodiment, the subject's immune system is depleted or ablated by the administration of an induction chemotherapy regimen comprising a therapeutically effective amount of etoposide, doxorubicin, vincristine, cyclophosphamide, and prednisone (EPOCH). In another embodiment, fludarabine can also be administered to improve the depletion of T cells.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

The following example is for the purpose of illustration only and is not intended to limit the scope of the claims, which are appended hereto.

Example 1: Tumor-Specific IL-9-Producing CD8+ Tc9 Cells are Superior Effector than Type-I Cytotoxic Tc1 Cells for Adoptive Immunotherapy of Cancers $CD8^+$ CTLs are thought to play a crucial role in tumor rejection, and extensive focus has been devoted to the study of $CD8^+$ T cells in adoptive transfer protocols. Nevertheless, complete and durable tumor regression or cure rates remains to be archived. In the current study, we identified unique IL-9-skewed $CD8^+$ T cells, termed Tc9 cells, by priming with Th9-polarized condition. Apart from the differences in cytokine secretion, Tc9 cells differed from Tc1 cells in that they were less cytotoxic in vitro. The existence of a Tc9 cell subset in both cultured system and in vivo has been shown. However, the role of this $CD8^+$ T-cell subset has not been tested in cancer immunotherapy settings. In this study, we evaluated the efficacy of Tc9 cell transfer in both OT-I/B16-OVA and Pmel-1/B16 mouse models in comparison with the classic Tc1 cells. We demonstrate that transfer of Tc9 cells displayed superior efficacy to mediate regression of large established tumors by converting to IFN-γ-producing cytolytic effector cells in vivo.

IL-9-Producing Tc9 Cells are Skewed Away from IFN-γ Production and Cytolytic Phenotype.

Figure 12:
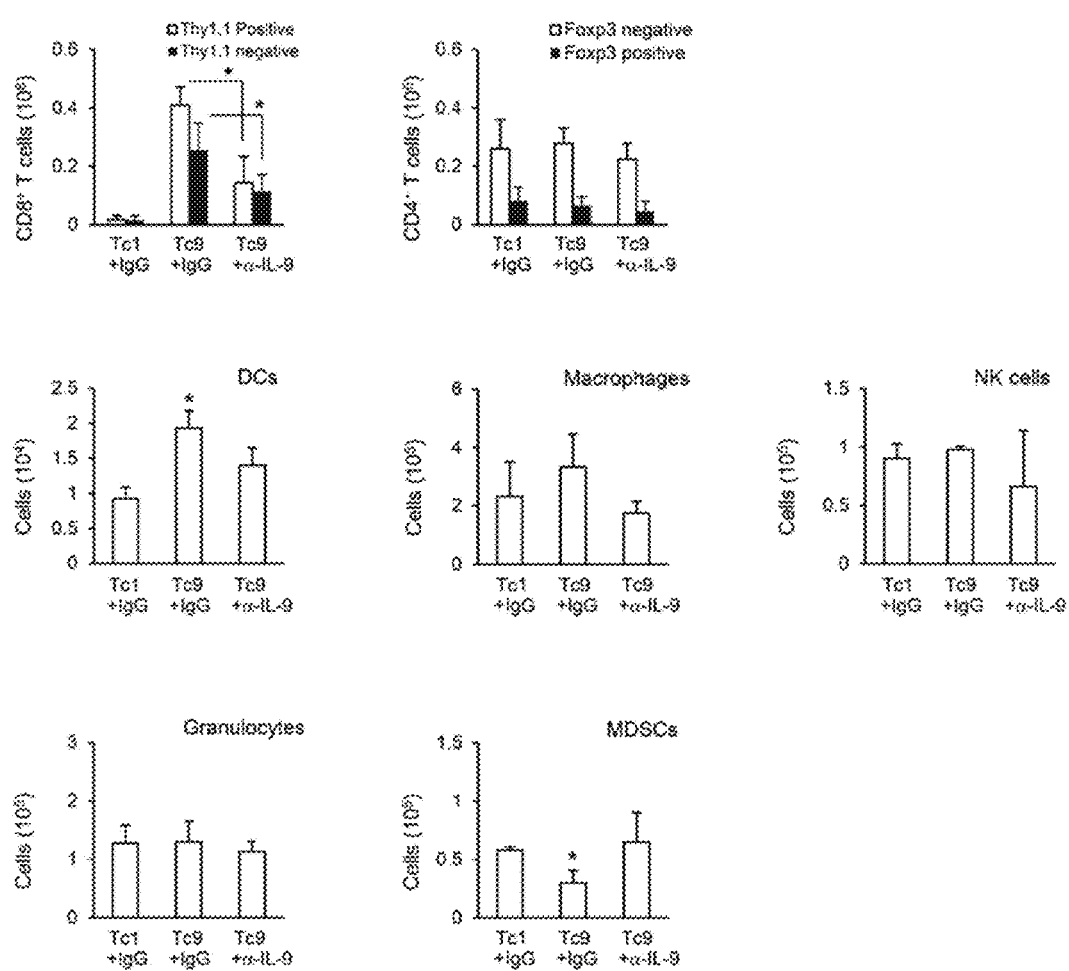
FIG. 12 is a series of graphs illustrating the results of a cytotoxicity assay. T cells were added at the indicated ratios to CFSE$^{hi}$ B16-OVA target cells or CFSE$^{lo}$ B16 non-target cells in duplicate. Percent of specific lysis was determined after 8 hours. Representative results from one of two performed experiments are shown.

We first investigated the effect of Th9-polarization conditions on the antigen-driven acquisition of an IL-9-producing Tc9-cell phenotype. Similar to the cytokine profile of Th9 cells, IL-9-skewed CD8+ T cells demonstrated diminished mRNA expression of Ifng but enhanced expression of Il9 and Il2, which were associated with diminished expression of cytolytic molecules, such as GrzB and Perforin (FIG. 1A). The expression of Eomes and Tbx21, the transcriptional master regulators that confer cytolytic lymphocyte lineage characteristics, were substantially suppressed in IL-9-skewed CD8+ T cells (FIG. 1B). However, the expression of Irf4 and Pu.1, two transcription factors governing Th9-cell lineage development, was significantly up-regulated in Tc9 cells (FIG. 1B). The suppressed expression of CTL hallmark molecules, such as GrzB, Perforin, Eomes, and Tbx21, suggested the impaired CTL development of Tc9 cells and possibly diminished cytotoxicity. Indeed, OT-I Tc1 cells showed strong cytotoxicity against tumor target cells, whereas OT-I Tc9 cells exhibited minimal specific cytolytic activity (FIG. 1C and FIG. 12). Therefore, compared with IL-2-primed IFN-γ-producing cytolytic Tc1 cells, IL-9-skewed Tc9 cells were diverted from the classic cytolytic phenotype.

Characterization of Tc9 Cytokine Expression Profiles.

Figure 2:
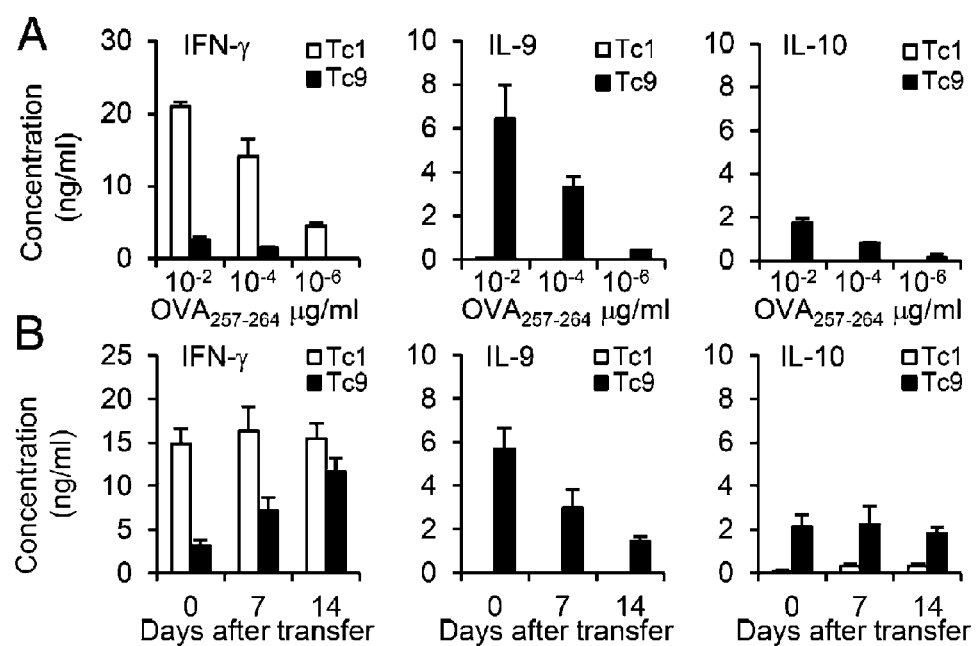
FIG. 2 illustrates the cytokine expression profile of Tc9 cells; (A) is a series of graphs showing OT-I Tc1 or Tc9 cells primed in polarized conditions and expanded with IL-2. The cells were then restimulated with splenocytes pulsed with $OVA_{257-264}$ at indicated concentrations for 24 h. Production of indicated cytokines was determined by ELISA; (B) is a series of graphs showing OT-I Tc1 or Tc9 cells ($2\times10^6$) adoptively transferred into CD45.1-transgenic mice, followed by i.v. injection of $5\times10^5$ $OVA_{257-264}$-pulsed DCs and i.p. injection of four doses of exogenous IL-2. $CD45.2^+$ transferred cells were sorted from splenocytes at days 7 and 14. Day 0 represents T cells before transfer. The cells were then restimulated with splenocytes pulsed with 0.01 μg/mL $OVA_{257-264}$ in triplicate for 24 h. Production of indicated cytokines was determined by ELISA. Representative results from one of two repeated experiments are shown.
Figure 13:
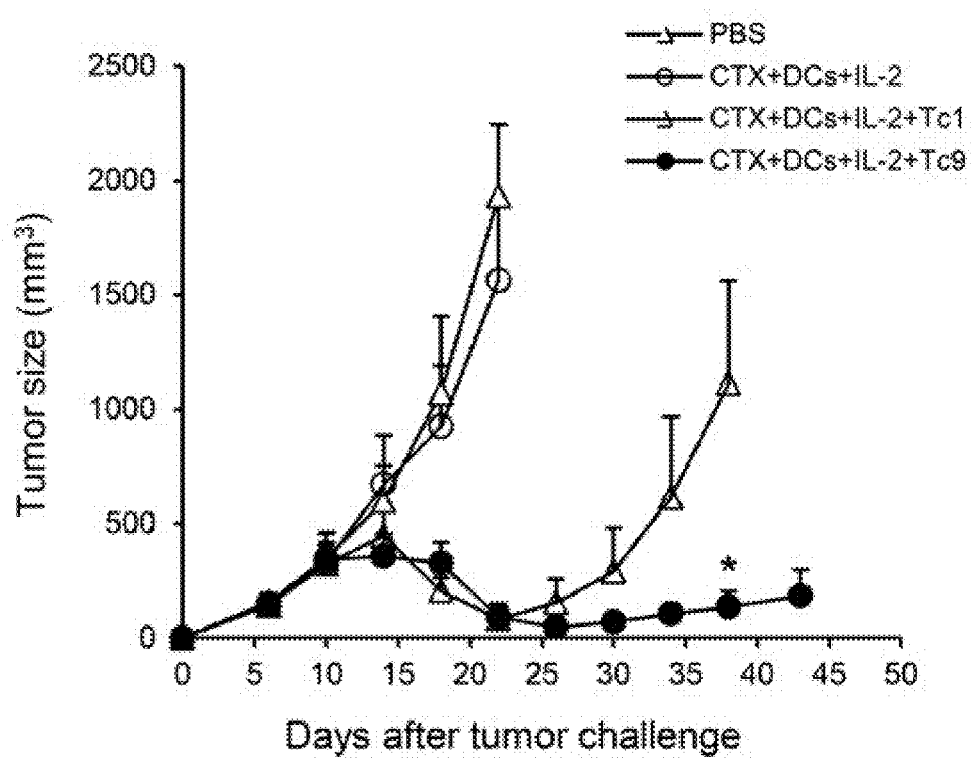
FIG. 13 illustrates the production of IL-4 and IL-17 by Tc1 and Tc9 cells; (A) is a pair of graphs showing OT-I Tc1 or Tc9 cells primed in polarized conditions and expanded with IL-2. The cells were then restimulated with splenocytes pulsed with OVA$_{257-264}$ at indicated concentrations for 24 hours. Production of indicated cytokines was determined by ELISA; (B) is a pair of graphs showing OT-I Tc1 or Tc9 cells ($2\times10^6$) adoptively transferred into CD45.1-transgenic mice, followed by i.v. injection of $5\times10^5$ OVA$_{257-264}$-pulsed DCs and i.p. injection of 4 doses of exogenous IL-2. CD45.2+ transferred cells were sorted from splenocytes at days 7 and 14. Day 0 represents T cells before transfer. The cells were then restimulated with splenocytes pulsed with 0.01 µg/ml OVA$_{257-264}$ in triplicate for 24 hours. Production of indicated cytokines was determined by ELISA. Representative results from one of two repeated experiments are shown.

To determine the specific cytokine expression patterns of IL-9-skewed Tc9 cells, we measured by ELISA the cytokine production after restimulation. As expected, OT-I Tc1 cells produced a large amount of IFN-γ, whereas Tc9 cells released a minimal amount of IFN-γ but secreted a large amount of IL-9 (FIG. 2A). In addition, these Tc9 cells also produced some IL-4, IL-10, and IL-17 after in vitro restimulation (FIG. 2A and FIG. 13A). In contrast, production of IL-9, IL-4, IL-10, or IL-17 from Tc1 cells was undetectable, suggesting distinct expression patterns between Tc1 and Tc9 cells.

To further test the cytokine expression profile of Tc9 cells, we transferred CD45.2+ OT-I Tc1 or Tc9 cells into CD45.1 transgenic mice followed by OVA peptide-pulsed dentritic cell (DC) vaccination and four daily doses of rhIL-2 to boost the antitumor responses of ACT in vivo. CD45.2+CD8+ T cells were sorted from splenocytes 7 and 14 d after transfer, and cytokine production was measured after in vitro restimulation. Compared with cells before transfer, Tc1 cells continued to produce similar amounts of IFN-γ without other cytokines examined. Noticeably, IL-9 production from Tc9 cells was decreased over time after transfer, and these cells were converted to IFN-γ-producing Tc1-like cells especially at day 14 after transfer (FIG. 2B). In addition, Tc9 cells kept IL-10 production in vivo, whereas IL-4 and IL-17 secretion was reduced over time (FIG. 2B and FIG. 13B). These results revealed that Tc9 cells are unstable and flexible in cytokine production in vivo, and suggested that Tc9 cells could gain the ability to produce IFN-γ and might further differentiate into fully cytolytic effector cells after transfer.

OVA-Specific Tc9 Cells Eradicate Large Established B16-OVA Melanoma.

Figure 3:
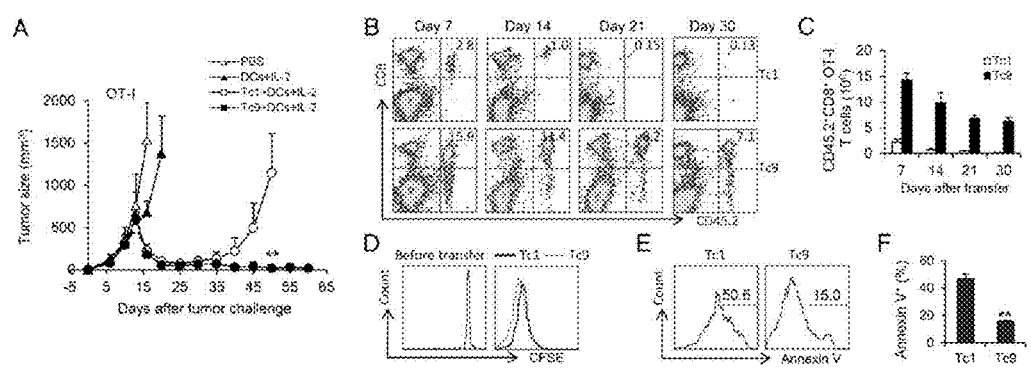
FIG. 3 illustrates that OT-I Tc9 cells mediated enhanced antitumor response and displayed greater persistence; (A-C) is a series of graphs and histograms showing that Tc1 or Tc9 cells ($2\times10^6$) were adoptively transferred into CD45.1-transgenic mice bearing 10-d large established B16-OVA melanoma. DC vaccination and IL-2 were administered to some group of mice as indicated; (A) shows tumor responses (n=5) to adoptive transfer of Tc1 or Tc9 were shown; (B and C) show persistence of transferred Tc1 or Tc9 cells in the spleens of treated tumor-bearing mice was analyzed by FACS. Numbers in histograms (B) represent the percentage of $CD45.2^+CD8^+$ OT-I T cells in splenocytes. (C) Total number of $CD45.2^+CD8^+$ OT-I T cells was calculated from B. The spleens of three mice per condition were examined at each time point; (D) is graph showing that CFSE-labeled Tc1 or Tc9 cells were transferred into tumor-bearing mice. Shown is CFSE dilution of gated $CD45.2^+CD8^+$ splenocytes 4 d after transfer; (E and F) are graphs showing Annexin V expression was measured in Tc1 and Tc9 cells 4 d after transfer. (E) Numbers in histograms represent the percentage of Annexin V$^+$ apoptotic Tc1 or Tc9 cells in splenocytes. Summarized (n=3) percentages of apoptotic transferred cells were shown in F. Representative results from one of two repeated experiments are shown. **P<0.01.
Figure 7:
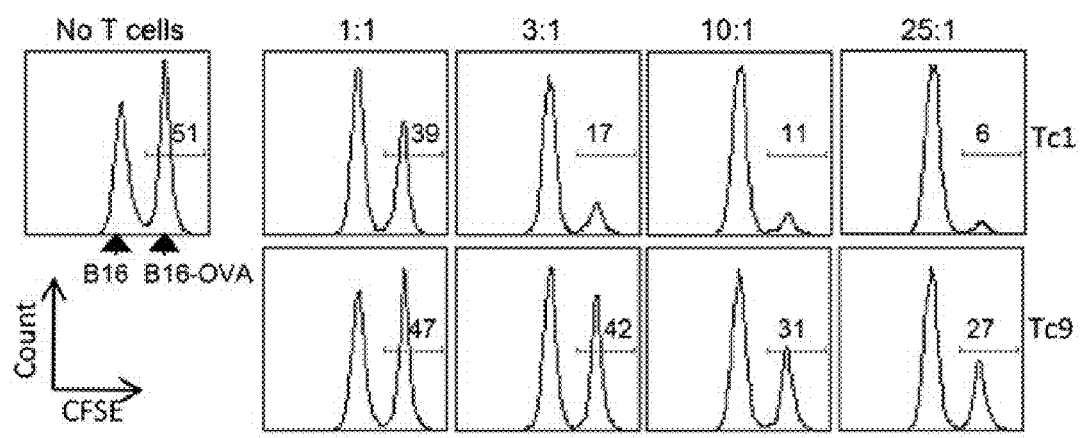
FIG. 7 illustrates T cell-treatment protocols; (A) is an illustration showing mice injected s.c. in the front abdomen with 6×10$^5$ B16-OVA tumor cells. At 10 days after tumor injection, mice (5/group) were treated with adoptive transfer of 2×10$^6$ OT-I Tc1 or Tc9 cells, followed by i.v. injection of 5×10$^5$ peptide-pulsed DCs. rhIL-2 was given at 6×10$^5$ U i.p. daily for 4 doses after T-cell transfer; (B) is an illustration showing mice were injected s.c. in the front of the abdomen with 6×10$^5$ B16 or MC38-gp100 tumor cells. CTX was administered i.p. as a single dose of 250 mg/kg 1 day before T-cell transfer. At 10 days after tumor injection, mice (5/group) were treated with adoptive transfer of 2×10$^6$ Pmel-1 Tc1 or Tc9 cells, followed by i.v. injection of 5×10$^5$ peptide-pulsed DCs. rhIL-2 was given at 6×10$^5$ U i.p. daily for 4 doses after T-cell transfer.

To assess whether the phenotypic differences between Tc1 and Tc9 cells would translate into different efficacy after transfer in vivo, we treated B16-OVA-bearing CD45.1-transgenic mice with equal numbers of adoptively transferred OT-I Tc1 or Tc9 cells, followed by DC vaccination and four daily doses of rhIL-2. To mimic a clinically relevant scenario, tumors were allowed to grow for 10 d before the treatment (FIG. 7A). Surprisingly, only Tc9 cells mediated a significant tumor regression resulting in a complete cure and long-term survival, whereas Tc1 cell-treated mice relapsed 4 wk after T-cell infusion despite the initial tumor shrinkage within the first 3 wk (FIG. 3A). To better understand the differences between Tc1 and Tc9 cells in treatment outcomes, we analyzed spleens after T-cell infusion for the presence of adoptively transferred effector cells. Flow cytometry analysis revealed that the percentages and absolute numbers of CD45.2+CD8+ splenocytes from Tc9 cell-treated mice were consistently higher than Tc1 cell-treated mice over time (FIGS. 3B and C). Further evaluation by carboxyfluorescein succinimidyl ester (CFSE) dilution assay demonstrated that on the fourth day, CFSE intensity of Tc1 and Tc9 cells in spleens was similar, suggesting that both cells proliferated well in the mice (FIG. 3D). In contrast, Tc1 cells recovered on the fourth day had significantly higher percentages of Annexin V+ apoptotic cells in spleens compared with Tc9 counterparts (FIGS. 3E and F). These results suggested that the persistence of Tc9 cells, which might be one of the key reasons for the rejection of established tumor after transfer, may be the result of a survival advantage or resistance to apoptosis rather than increased proliferation of the cells.

Tc9 Cells are Less Exhausted and Developed into Full Effector Cells In Vivo.

Driven by elevated levels of T-bet, Tc1 cells become terminally differentiated short-lived effector cells with KLRG-1$^{high}$ and IL-7Rα$^{low}$ phenotype. However, compared with Tc1 counterparts, the tumor-specific Tc9 cells expressed significantly higher levels of IL-7Rα, a prosurvival cytokine receptor, suggesting a possible mechanism of the increased persistence of these cells (FIG. 4A). Furthermore, Tc9 cells had significantly down-regulated expression of the exhaustion markers, such as KLRG-1, PD-1, LAG3, and 2B4 (FIG. 4B), demonstrating that Tc9 cells were less exhausted T cells even upon repeated activation in vivo. Reciprocally, Tc1 cells acquired a signature of terminal differentiation with high expression of exhaustion-phenotypic markers, leading to the failure of homeostatic proliferation, dysfunction, and apoptosis of these cells (FIG. 4B). As less exhausted T cells, the long-term survival of Tc9 cells also allowed them to convert to IFN-γ-positive Tc1-like cells especially 14 d after transfer, which was accompanied by a decrease of IL-9-producing CD8+ T cells (FIG. 4C). By calculating the total number of IFN-γ-positive Tc1-like transferred cells, we found that Tc9 cell-transferred mice had already developed more than twofold Tc1-like cells compared with those in Tc1 cell-transferred mice 7 d after the transfer and this ratio kept increasing over time (FIG. 4D). Because production of IFN-γ is a quintessential characterization of cytolytic CD8+ T cells, we analyzed and calculated GrzB-producing CD8+ T cells from tumor-bearing mice. We enumerated significantly more GrzB-positive Tc9-derived cells than those in Tc1-cell transferred mice (FIGS. 4E and F). These results showed that Tc9 cells could evolve in vivo into distinct Tc1-like effector cells, which might be responsible for the Tc9 cell-mediated tumor destruction.

Cyclophosphamide Synergizes with Pmel-1-Derived Tc9 Cells To Mediate Enhanced Antitumor Immunity.

Because OT-I cells target artificial antigen, we next used the Pmel-1 model of adoptive immunotherapy, which reproduces the clinical challenge of targeting gp100 tumor/self-antigen in the poorly immunogenic B16 melanoma. One day before T-cell adoptive transfer, mice were given one dose of cyclophosphamide (CTX; 250 mg/kg), which can induce lymphopenia, sensitize tumor cells to immune destruction, and promote homeostatic proliferation of transferred T cells. Tc1 or Tc9 cells were transferred into mice bearing large established B16 melanoma in conjunction with DC vaccination and four daily doses of rhIL-2 (FIG. 7B). Noticeably, Tc9-cell transfer mediated sustained antitumor responses throughout the experiment, whereas Tc1 cells only induced temporary tumor regression, which was followed by relapse of aggressive tumor growth (FIG. 5A). In addition, the development of autoimmune vitiligo was apparent 4 wk after transfer of Tc9 cells but was not observed in any of Tc1 cell-treated mice (FIG. 5B).

This Pmel-1 Tc9 cell-mediated sustained antitumor response was also associated with superbly improved in vivo expansion and persistence of the transferred cells examined in the spleen of the tumor-bearing mice (FIG. 5C). Intracellular staining revealed that, similar to OT-I Tc9 cells, transfer of Pmel-1 Tc9 cells also developed into large numbers of IFN-γ-positive Tc1-like cells and GrzB-positive cytolytic effector cells (FIGS. 5D and E). We further measured the cytokine production by transferred cells isolated from the spleens and tumor tissues of tumor-bearing mice. ELISA results indicated that Tc1 cells maintained IFN-γ and TNF-α production in the spleens, but the production of these cytokines was significantly decreased in tumor tissues (FIG. 5F). In contrast, Tc9 cells gained the ability to produce IFN-γ and TNF-α in vivo, and tumor-infiltrating Tc9 cells maintained the production of these cytokines compared with Tc9 cells in the spleens. Notably, only Tc9 cells produced significant amounts of IL-9 and IL-2, which indicated a less differentiated phenotype of Tc9 cells. By comparing the cytotoxicity of these sorted cells, we found that tumor-infiltrating Tc1 and Tc9 cells were similar in their ability to lyse target tumor cells, although splenic Tc1 cells had slightly higher cytotoxicity than Tc9 cells (FIG. 5G). Collectively, Pmel-1 Tc9-cell transfer confers effective antitumor response against large B16 melanoma, and the failure of Tc1 cells to control the disease might be due to the inability of these cells to expand and persist despite the higher cytotoxicity and ability to secrete IFN-γ in vitro and in vivo.

Therapeutic Effect of Tc9 Cells Critically Depends on IL-9.

Figure 6:
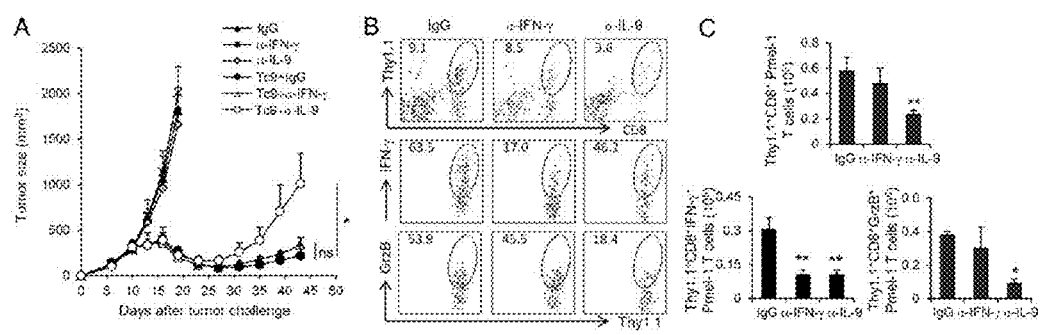
FIG. 6 illustrates that IL-9 contributes to Tc9 cell-mediated tumor rejection. Pmel-1 Tc9 cells (2×10$^6$) were adoptively transferred into C57BL/6 mice bearing 10-d large established MC38-gp100 tumor. One dose of CTX was given 1 d before T-cell transfer. DC vaccination and IL-2 were administered to the mice that received T-cell transfer. mAbs neutralizing IL-9 or IFN-γ or control IgG were i.p. injected to mice as indicated. (A) is a graph showing tumor responses (n=5) to adoptive transfer of Tc9 and antibody treatment were shown; (B) is a series of histograms showing a FACS determination of the percentage of tumor-infiltrating, adoptively transferred Thy1.1$^+$CD8$^+$ T cells, IFN-γ-producing or GrzB-producing tumor-infiltrating, adoptively transferred Thy1.1$^+$CD8$^+$ T cells in the leukocyte fraction. Tumor tissues were harvested 3 wk after transfer; (C) is a series of bar graphs showing the total number of tumor-infiltrating, IFN-γ-producing or GrzB-producing Thy1.1$^+$CD8$^+$ T cells 3 wk after transfer was calculated from FACS analysis. Cell number was normalized to 500-mg tumor tissues. Representative results from one of two performed experiments are shown. *P<0.05; **P<0.01.
Figure 8:
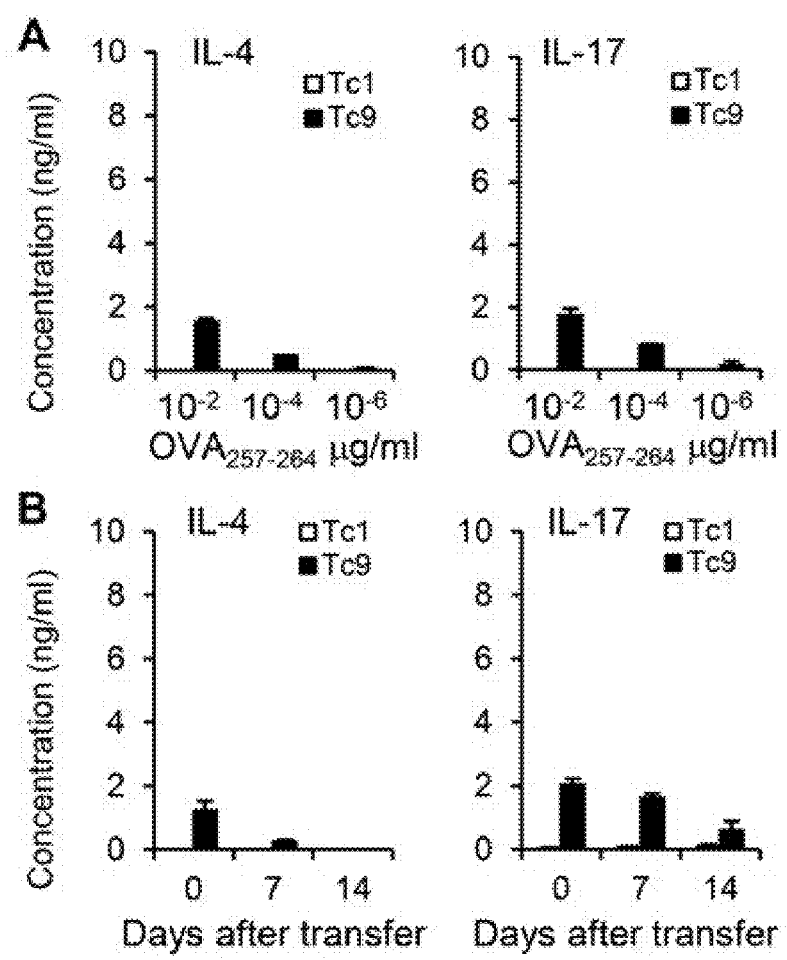
FIG. 8 is a pair of graphs illustrating that the transfer of Tc9 cells mediated enhanced antitumor response than Tc1 and naïve CD8+ T cells in large established MC38-gp100 tumor model. Pmel-1 Tc9, Tc1 or naïve CD8+ T cells (2×10$^6$) were adoptively transferred into C57BL/6 mice bearing 10-day large established MC38-gp100 tumor. One dose of CTX was given 1 day before T-cell transfer. DC vaccination and IL-2 were administered to the mice. Tumor responses (left; N=5) to adoptive transfer of T cells and total number of splenic Thy1.1+CD8+ T cells calculated from FACS analysis (right; N=3; 3 weeks after transfer) are shown. *P<0.05.
Figure 9:
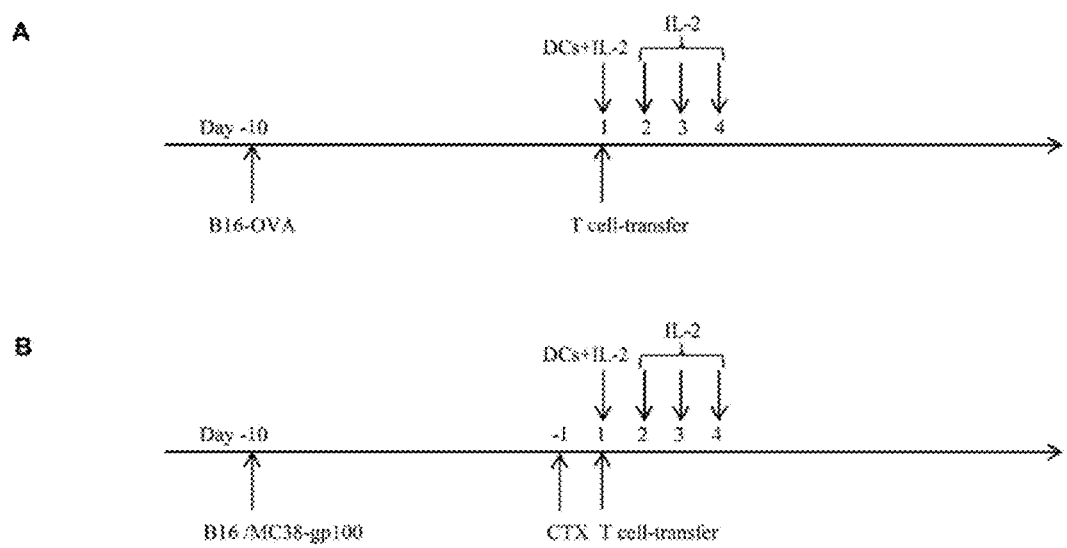
FIG. 9 is a series of graphs illustrating that antibody treatment did not influence the persistence of transferred Tc9 cells. Pmel-1 Tc9 cells (2×10$^6$) were adoptively transferred into C57BL/6 mice bearing 10-day large established MC38-gp100 tumor. One dose of CTX was given 1 day before Tcell transfer. DC vaccination and IL-2 were administered to the mice that received T-cell transfer. mAbs neutralizing IL-9 or IFN-γ or control IgG were i.p. injected to mice as indicated. Total number of IFN-γ- or GrzB-producing Thy1.1+CD8+ T cells in the spleens 3 weeks after transfer was calculated from FACS analysis. Representative results from one of two performed experiments are shown. *P<0.05.
Figure 10:
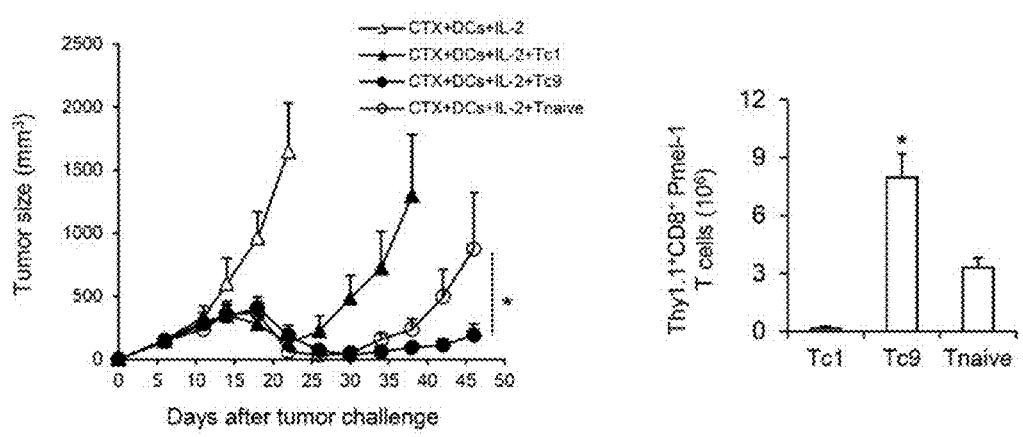
FIG. 10 is a series of graphs illustrating the effects of Tc9-cell transfer on the recruitment of immune cells into tumor tissues. Pmel-1 Tc9 or Tc1 cells (2×10$^6$) were adoptively transferred into C57BL/6 mice bearing 10-day large established MC38-gp100 tumor. One dose of CTX was given 1 day before T-cell transfer. DC vaccination and IL-2 were administered to the mice that received Tcell transfer. mAbs neutralizing IL-9 or control IgG were i.p. injected to mice as indicated. Total number of tumor-infiltrating, Thy1.1+CD8+ T cells, Thy1.1− CD8+ T cells, CD4+ effector T cells (CD4+Foxp3−), regulator T cells (CD4+Foxp3+), DCs (CD11c+), macrophages (F4/80+), NK cells (NK1.1+), granulocytes (Gr-1+CD11b−) and MDSCs (Gr-1+CD11b+) 3 weeks after transfer was calculated from FACS analysis. Cell number was normalized to 500 mg tumor tissues. Representative results from one of two performed experiments are shown. *P<0.05.
Figure 11:
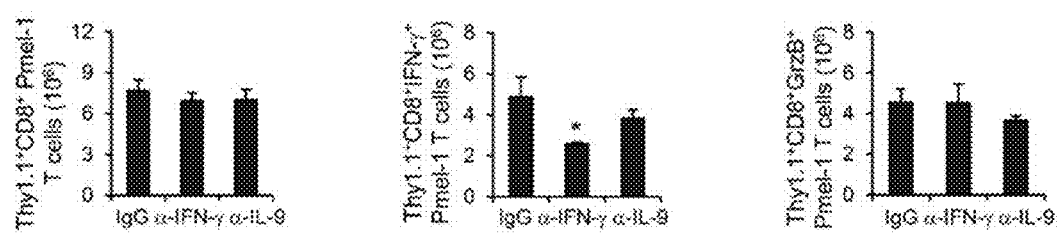
FIG. 11 is a graph illustrating that endogenous host B or T lymphocytes are not required for the Tc9 cell-mediated sustained antitumor response. Pmel-1 Tc9 or Tc1 cells ($2\times10^6$) were adoptively transferred into C57BL/6 Rag-1$^{-/-}$ mice bearing 10-day large established MC38-gp100 tumor. One dose of CTX was given 1 day before T-cell transfer. DC vaccination and IL-2 were administered to the mice as indicated. Tumor responses (N=5) to adoptive transfer of T cells are shown. Representative results were obtained from one of two performed experiments. *P<0.05.

Because Tc9 cells acquired the ability to secrete IFN-γ in tumor-bearing mice, we next determined the importance of Tc9-derived IFN-γ and IL-9 in mediating tumor rejection in MC38-gp100 tumor model. In this model, transfer of Pmel-1 Tc9 cells could mediate significantly enhanced antitumor response than that of Pmel-1 Tc1 or naïve CD8+ T cells, which was associated with a superior persistence of Tc9 cells in recipient mouse spleens (FIG. 8). We treated MC38-gp100 tumor-bearing mice with isotype controls, IL-9-neutralizing antibodies or IFN-γ-neutralizing antibodies and subsequently transferred them with Pmel-1 Tc9 cells. Unexpectedly, tumor rejection was abrogated only by anti-IL-9 treatment, whereas neutralizing IFN-γ did not reach statistical significance compared with isotype control (FIG. 6A). By calculating the absolute numbers of splenic Thy1.1+CD8+ cells in treated mice, we found that IL-9 neutralization did not impair the persistence of Tc9 cells or their ability to produce IFN-γ and GrzB (FIG. 9). However, in IL-9-neutralized mice, the number of tumor-infiltrating Thy1.1+CD8+ T cells were substantially reduced compared with those in mice receiving isotype control or anti-IFN-γ antibodies. This impaired Thy1.1+CD8+ T-cell infiltration could also be demonstrated by the sharply decreased numbers of IFN-γ-producing and GrzB-producing Thy1.1+CD8+ cells recovered from tumor sites (FIGS. 6B and C). On the other side, anti-IFN-γ treatment only ablated the production of IFN-γ from transferred Tc9 cells, whereas the homing of cytolytic Tc9 cells to tumor tissues was not affected (FIGS. 6B and C). In addition, by examining the leukocyte subsets in tumor microenvironment, we also observed significantly increased IL-9-dependent tumor-infiltrating host Thy1.1-CD8+ T cells in Tc9 cell-transferred mice (FIG. 10). Because Tc9-cell transfer mediated a sustained antitumor response in C57BL/6 Rag-1$^{-/-}$ mice similar to that in wild-type mice, host CTL responses may have contributed, but were not required, for the antitumor efficacy of Tc9 cells in vivo (FIG. 11). Taken all together, these results illustrate that Tc9 cells kilsl tumor cells independent of their secreted IFN-γ, possibly by using the cytolytic enzymes, and IL-9 provided critical help to their migration into tumor sites to exert effector function.

Materials and Methods

Mice and Cell Lines

C57BL/6 mice were purchased from the NCI, and OT-I (C57BL/6-Tg(TcraTcrb)1100 Mjb/J), Pmel-1 (B6.Cg Thy1$^a$-Tg(TcraTcrb)8Rest/J), CD45.1 (B6.SJL-Ptprca Pepcb/BoyJ) and Rag-1$^{-/-}$ (B6.129S7-Rag1$^{tm1Mom}$/J) mice were purchased from the Jackson Laboratory. All mice were 6 to 8 weeks old at the beginning of each experiment. The wild-type B16 or B16 transfected with OVA (B16-OVA) melanoma cell lines and wild-type MC38 or MC38 transfected with hgp100 (MC38-gp100) (1) colon adenocarcinoma cell lines were cultured in Iscove's modified Dulbecco's media (IMDM;Invitrogen) supplemented with 10% heat-inactivated fetal bovine serum (Thermo Scientific), 100 U/mL penicillin-streptomycin, and 2 mM L-glutamine (both from Invitrogen).

In Vitro Tc1 and Tc9 Cell Differentiation

Tc9 cell differentiation was accomplished by priming OT-1/CD45.2 or Pmel-1/Thy1.1 naïve CD8$^+$CD62L$^+$ T cells with irradiated peptide-loaded splenic APCs in the presence of Th9-polarized medium supplemented with IL-4 (10 ng/ml; R&D Systems), TGF-β (1 ng/ml; R&D Systems), anti-IFN-γ monoclonal antibodies (mAbs; 20 μg/ml; eBioscience) and anti-IL-12 mAbs (10 μg/ml; eBioscience). Beginning 2 days after priming, cell cultures were expanded in fresh Th9-polarized medium supplemented with 50 ng/ml IL-2 (50 ng/ml; R&D Systems) for additional 3 days before tests or transfer. Tc1 was primed with peptide supplemented with 100 ng/ml rhIL-2 and expanded with 50 ng/ml IL-2 for additional 3 days. In some experiments, cells were restimulated for 5 hours with peptide-pulsed T cell depleted splenocytes in the presence of GolgiPlug (BD Biosciences) before intracellular staining using a Cytofix/Cytoperm kit (BD Biosciences). Cytokine levels in supernatants were measured by ELISA kits (Peprotech).

Real-Time PCR

Total RNA was extracted from Tc1 or Tc9 cells by using RNeasy Mini kit (Qiagen) according to the manufacturer's instruction. The expression of Ifng, Il9, Il2, Grzb, Perforin, Eomes, Tbx21, Pu.1 and Irf4 was performed using well known primers and analyzed by using SYBR green real-time PCR (Applied Biosystems). Expression was normalized to the expression of the housekeeping gene Gapdh.

Tumor Models and Adoptive Transfer

Mice were injected s.c. in the front of the abdomen with 6×105 B16, B16-OVA or MC38-gp100 tumor cells. At 10 days after tumor injection, mice (5/group) were treated with adoptive transfer of 2×10$^6$ Tc1 or Tc9 cells, followed by i.v. injection of 5×10$^5$ peptide-pulsed bone marrow-derived dendritic cells (DCs). rhIL-2 was given at 6×10$^5$ U i.p. daily for 4 doses after T-cell transfer. As indicated, CTX (Sigma-ALdrich) were administrated i.p. as a single dose at 250 mg/kg 1 day before T-cell transfer. Some of the mice were given i.p. injection of 300 μg anti-IFN-γ or anti-IL-9 mAbs (Bio X Cell) every 3 days starting at one day before transfer. Mice were sacrificed at indicated days, and splenocytes were analyzed. The number of transferred cells, IFN-γ-producing or GrzB-producing transferred cells in spleens of treated mice were calculated by multiplying the total number of viable splenocytes by the frequency the indicated populations. In some experiments, transferred T cells were sorted from splenocytes or tumor tissue for indicated tests.

Flow Cytometry

FITC-, PE, APC or PerCP-conjugated mAbs against CD45.2, Thy1.1, CD8, IL-7Rα, KLRG1, PD-1, LAG-3, 2B4, IL-9, IFN-γ, GrzB, Foxp3, CD11c, CD11 b, F4/80, NK1.1, Gr-1 and Annexin V (all from eBioscience) were used for staining after Fc blocking, and analyzed using a FACS Calibur flow cytometer.

CFSE Labeling and Cytotoxicity Assay

In some experiments, Tc1 or Tc9 T cells were incubated for 5 minutes at 37° C. with 1 μM CFSE in PBS, and then washed extensively before transfer. In cytotoxicity assay, B16-OVA target cells for OT-I T cells were labeled with 5 μM CFSE, whereas B16 nontarget cells were labeled with 0.5 μM CFSE as control. B16-OVA target cells or B16 non-target control cells were incubated alone in duplicate with the OT-I CD8+ T cells at different effector to target ratios as indicated. After 8 hours, cells from each target and control well were mixed and analyzed by FACS. Percent specific lysis was calculated as (1-tragets/control)×100%. For determination of cytotoxicity of Pmel-1 cells, B16 target cells were labeled with 5 μM CFSE, whereas MC38 non-target cells were labeled with 0.5 μM CFSE as control.

Statistical Analysis

For statistical analysis, 2 tailed Student's t-test was used. A P value less than 0.05 was considered statistically significant. Results are typically presented as means±SD.

From the above description of the application, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

Having described the invention, the following is claimed:

1. A method of treating cancer in a subject comprising administering to the subject a therapeutically effective amount of a population of CD8+ Tc9 cells and a pharmaceutically acceptable carrier, wherein the population of CD8+ Tc9 cells secretes IL-9, wherein the CD8+ Tc9 cells are produced by priming a population of naïve CD8+ T cells by contacting the population of naïve CD8+ T cells with an immunogenic peptide, in the presence of a first Tc9 supportive environment, thereby producing a population of CD8+ Tc9 lymphocytes which secrete IL-9, wherein the first Tc9 supportive environment comprises at least one Tc9 polarizing cytokine or agent selected from the group consisting of IL-4, TGF-β, INF-γ neutralizing agent and IL-12 neutralizing agent.

2. The method of claim 1, wherein the subject is a human.

3. The method of claim 1, wherein the CD8+ Tc9 cells are produced from a population of autologous naïve CD8+ T cells.

4. The method of claim 1, wherein the first Tc9 supportive environment comprises about 1 ng/ml to about 100 ng/ml of IL-4, about 0.1 ng/ml to about 10 ng/ml of TGF-β, about 1 μg/ml to about 100 μg/ml of anti-INF-γ monoclonal antibodies, and about 1 μg/ml to about 100 μg/ml of anti-IL-12 monoclonal antibodies.

5. The method of claim 1, further comprising allowing the primed population of CD8+ Tc9 lymphocytes to proliferate in a second Tc9 supportive environment before administering the population of cells to the subject, wherein the second Tc9 supportive environment comprises about 1 ng/ml to about 100 ng/ml of IL-2.

6. The method of claim 1, wherein the immunogenic peptide is presented on irradiated immunogenic peptide-loaded dendritic cells.

7. The method of claim 1, wherein the cancer is selected from the group consisting of gastrointestinal cancer, ovarian cancer, breast cancer, head and neck cancer, lung cancer, cancer of the nervous system, kidney cancer, retinal cancer, melanoma, stomach cancer, liver cancer, pancreatic cancer, genital-urinary cancer, colorectal cancer, and bladder cancer.

8. The method of claim 1, wherein the cancer is a selected from colorectal cancer and melanoma.

9. The method of claim 1, wherein the population of CD8+ Tc9 cells is administered to the subject intravenously.

10. The method of claim 1, further comprising the administration of a chemotherapeutic agent to the subject.

11. The method of claim 10, the chemotherapeutic agent comprising cyclophosphamide.

* * * * *